US006509175B2

(12) United States Patent
Fu et al.

(10) Patent No.: US 6,509,175 B2
(45) Date of Patent: Jan. 21, 2003

(54) CDNA LIBRARIES AND METHODS FOR THEIR PRODUCTION

(75) Inventors: Glenn K. Fu, Dublin, CA (US); Laura L. Stuve, Los Gatos, CA (US); Walter H. Lee, Campbell, CA (US); Irene Ni, San Leandro, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/833,498

(22) Filed: Apr. 11, 2001

(65) Prior Publication Data

US 2002/0150899 A1 Oct. 17, 2002

(51) Int. Cl.[7] .......................... C12P 19/34; C12Q 1/68; G01N 33/00; C07H 21/02; C07H 21/04
(52) U.S. Cl. ................. 435/91.51; 435/6; 435/91.1; 435/91.2; 436/94; 536/23.1; 536/24.3; 536/24.33
(58) Field of Search .................... 435/6, 91.1, 91.2, 435/91.3, 91.51, 183; 436/94; 536/23.1, 24.3, 24.33, 25.3, 25.32, 25.4

(56) References Cited

U.S. PATENT DOCUMENTS

| 5,100,777 A | 3/1992 | Chang |
| 5,491,086 A | 2/1996 | Gelfand et al. |
| 5,866,395 A | 2/1999 | Mathur |
| 5,891,637 A | 4/1999 | Ruppert |
| 5,939,301 A | 8/1999 | Hughes, Jr. et al. |
| 5,948,614 A | 9/1999 | Chatterjee |
| 5,948,663 A | 9/1999 | Mathur |
| 6,001,645 A | 12/1999 | Slater et al. |
| 6,077,664 A | 6/2000 | Slater et al. |

OTHER PUBLICATIONS

Edmonds et al. (1971) "Polyadenylic Acid Sequences in the Heterogeneous Nuclear RNA and Rapidly–Labeled Polyribosomal RNA of HeLa Cells: Possible Evidence for a Precursor Relationship." *Proc. Natl. Acad. Sci. USA*, vol. 68(6):1336–1340.
Gubler et al. (1983) "A Simple and Very Efficient Method for Generating CDNA Libraries." *Gene*, vol. 25:263–269.
Kato et al. (1994) "Construction of A Full–Length CDNA Bank." *Gene*, vol. 150: 243–250.
Kotewicz et al. (1988) "Isolation of Cloned Moloney Murine Leukemia Virus Reverse Transcriptase Lacking Ribonuclease H Activity." *Nucleic Acids Research*, vol. 16(1):265–277.

*Primary Examiner*—Ethan C. Whigenant
*Assistant Examiner*—Frank Lu
(74) *Attorney, Agent, or Firm*—Bozicevic, Field & Francis, LLP; Carol L. Francis

(57) ABSTRACT

The present invention provides new methods of synthesizing cDNAs, methods of verifying full-length cDNAs, methods of producing cDNA libraries enriched for full-length inserts, and the like.

8 Claims, No Drawings

US 6,509,175 B2

CDNA LIBRARIES AND METHODS FOR THEIR PRODUCTION

FIELD OF THE INVENTION

The present invention relates to the construction of cDNA libraries, and in particular to methods of constructing full-length cDNA libraries.

BACKGROUND OF THE INVENTION

Methods for constructing complementary DNA (cDNA) libraries from mRNA are well known in the art. In a typical procedure, poly(A)+ mRNAs are isolated from cells, preferably a cell type in which the mRNA encoding the desired polypeptide is produced in large quantities. The mRNAs are then converted into cDNA in vitro using the enzyme reverse transcriptase to synthesize complementary cDNA strands from the mRNA template. General protocols are, for example, described in Chapter 5 of Ausubel et al., *Current Protocols in Molecular Biology*, Volume 1 (1991). Two commonly used methods of producing cDNA from mRNA are described in Okayama and Berg, *Mol. Cell Biol.* 2:161–170 (1982) and Gubler and Hoffman, *Gene* 25:263–269 (1983).

In the conventional process of converting mRNA into double stranded cDNA in vitro, a first cDNA strand is synthesized by the reverse transcriptase and separated from the mRNA by treatment with alkali or using a nuclease such as the enzyme RNase H. *E. coli* DNA polymerase then uses the first cDNA strand as a template for the synthesis of the second cDNA strand, thereby producing a population of double stranded cDNA molecules from the original poly (A)+ mRNA. After converting the 5' and 3' ends into blunt ends, the cDNA can be ligated to linkers/adaptors and subsequently ligated into suitable vectors and transformed or packaged into a cell line to form the library. The library can then be screened for cells transformed with nucleic acid encoding the desired polypeptide.

While the conventional methods have been used to successfully create cDNA libraries, and to identify a large number of polypeptides, they do have certain disadvantages. For example, an intrinsic problem in the construction of high quality full-length cDNA libraries is that, under in vitro conditions, the reverse transcriptase very often does not extend the first strand cDNA up to the 5' end of the mRNA, with the result that some mRNA sequences (often longer sequences) are not represented in the library. This is thought to occur in part due to misincorporation of an incorrect base by the reverse transcriptase, which destabilizes the cDNA/mRNA duplex. Enzymes or proteins present in the cell that normally repair nicks or correct mistakes during DNA synthesis are not present when the cDNA is synthesized in vitro.

In addition, hairpin formation in the mRNA can lead to early termination in the conversion to cDNA. This is especially a problem in the cloning of polypeptides having a signal sequence located at the 5' end of the gene, as these libraries are often screened by detecting polypeptide exported from the transformed cells. Thus, these methods require full-length cDNA, including the signal sequence.

A number of methods have been developed to attempt to address these problems. For example, a different method of synthesizing cDNA in vitro selects full length poly(A)+ mRNA by treatment with bacterial alkaline phosphatase and tobacco acid pyrophosphatase, and subsequently ligating the 5' end of the mRNA to a chimeric DNA-RNA linker containing a restriction site. See, Kato et al., *Gene* 25:243–250 (1994). The poly(A) 3' end of the mRNA is then hybridized to an oligo d(T) sequence of and the oligo d(T) used to prime cDNA synthesis. This procedure is also limited, however, by the efficiency of the phosphatases and the ligation procedure. Moreover, the ligation procedure can work with mRNA in which the 5' end has degraded, since the method does not distinguish between full-length and partial mRNA.

In standard methods currently used for the preparation of cDNA libraries, the mRNA in the cell is isolated by virtue of the presence of a polyadenylated tail present at its 3' end, which binds to a resin specific for this structure (oligo dT-chromatography). The purified mRNA is then copied into cDNA using a reverse transcriptase, which starts at the 3' end of the mRNA and proceeds towards the 5' end. Second strand synthesis is then performed. Linkers are added to the ends of the double stranded cDNA to allow for its packaging into virus or cloning into plasmids. At this stage, the cDNA is in a form that can be propagated.

One disadvantage observed with current cDNA library synthesis protocols is that current methods tend to produce libraries having a significant proportion of incomplete cDNAs, which results from inefficiencies in the reverse transcriptase employed to generate the library. To compensate for the incomplete cDNA constituents of the library, investigators must perform many rounds of isolation (screenings) and construct a "full-length" cDNA from the accumulated pieces. Such processes are resource intensive and do not ensure that each initial mRNA is represented in the cDNA library.

In addition, there is significant under-representation of sequences close to the 5' end of mRNAs in cDNA libraries produced by conventional methods. This under-representation results from the fact that the reverse transcriptase will usually "fall off" before reaching these sequences. In many instances, the information located at the 5' end is of great interest.

Thus, there remains a need in the art for improved cDNA libraries, and in particular for cDNA libraries that are enriched for full-length cDNAs.

SUMMARY OF THE INVENTION

The present invention provides methods for identifying cDNAs comprising sequences corresponding to the 5' end of a transcript, methods of producing libraries comprising cDNAs, methods of verifying the presence of a 5'-end in a cDNA, and producing libraries particularly rich in 5' ends and full length cDNAs (40–70%) relative to libraries produced from conventional technologies (10–30%).

In one embodiment, the present invention provides an improved method for producing full-length cDNAs comprising 1) relaxing the mRNA secondary structure, e.g., by adding an agent such as dimethyl sulfoxide (DMSO) to the first-strand synthesis reaction mixture and 2) utilizing a thermostable enzyme that exhibits 3' to 5' exonuclease activity for template driven enzymatic deoxynucleotide synthesis during first strand synthesis.

In one embodiment, the invention provides a method of isolating a full-length cDNA by: 1) contacting a ribonucleic acid molecule with a primer under conditions sufficient for template driven enzymatic deoxyribonucleic acid synthesis to occur to form a hybrid RNA:DNA molecule; 2) contacting the hybrid molecule with a detectably labeled oligo-dV primer under conditions sufficient for template driven enzymatic deoxyribonucleic acid synthesis to occur to produce hybrid primer:RNA sequences, provided the deoxyribonucleic acid of the first hybrid molecule does not extend to the 5' end of the ribonucleic acid; 3) isolating a hybrid molecule that does not contain label; and 4) converting the unlabelled hybrid molecule to a first double-stranded deoxyribonucleic acid molecule. In a particular embodiment, the single-stranded ribonucleic acid molecule is an mRNA. Following cDNA production, the double-stranded cDNA molecule can be introduced into a vector.

The primer used for first strand cDNA synthesis may be any primer that allows for directed synthesis of a deoxyribonucleic acid from a ribonucleic acid (including a gene specific primer and/or a random primer), but is preferably an oligo-dT primer. The detectably labeled oligo-dV primer can be labeled with anything known in the art, including but not limited to, biotin, digoxygenin, radioactivity, and the like.

The present invention also features a method of identifying a full-length first strand cDNA including the steps of contacting an RNA-cDNA hybrid with a detectably labeled primer under conditions sufficient for template driven enzymatic deoxyribonucleic acid synthesis to occur, where the primer is composed of a plurality of deoxyadenosines, deoxycytidines, and/or deoxyguanosines. The primer mixture used in the reaction may contain a plurality of the same primers, or a mixture of primers having varying sequences. The primer will result in primer:RNA hybrid sequences if the cDNA in the first hybrid molecule does not extend to the 5' end of the RNA, and the primers can be detected as labeled sequences in the RNA:cDNA hybrid. Labeled sequences in a hybrid is indicative of the hybrid having a non-full-length cDNA. This can be performed as a step in cDNA synthesis, or to verify the efficacy of a particular method and/or reagent (e.g., an enzyme).

Another embodiment provides a method for producing a 5' enriched cDNA library from a sample of mRNA molecules by: 1) contacting said mRNA molecules with a first primer under conditions sufficient for template driven enzymatic deoxyribonucleic acid synthesis to occur, creating a population of hybrid molecules of mRNA molecules hybridized cDNA molecules; 2) isolating the population of hybrid molecules; 3) contacting the isolated hybrid molecules with a detectably oligo-dV labeled primer under conditions sufficient for template driven enzymatic deoxyribonucleic acid synthesis to occur, so that the reaction results in additional production of hybrid sequences provided the cDNA in the first hybrid molecule does not extend to the 5' end of the ribonucleic acid; 4) isolating hybrid molecules that do not contain labeled primer sequences; and 5) converting the unlabeled hybrid molecules to a first double-stranded deoxyribonucleic acid molecule. These molecules can then be separated and introduced into vectors.

A feature of the present invention is a method for increasing the production of full-length cDNAs.

Another feature of the present invention is to provide methods for identifying cDNAs that comprise the 5' end of an RNA, and in particular the 5' end of an mRNA.

An advantage of the present invention is that it provides quick and effective methods for validating the presence of a 5' end on a cDNA.

Another advantage of the present invention is that it provides for improved full-length cDNA libraries.

These and other objects, advantages, and features of the invention will become apparent to those persons skilled in the art upon reading the details of the invention as more fully described below.

DETAILED DESCRIPTION OF THE PREFERRED EMBODIMENTS

Before describing the present methods, constructs and reagents, it is to be understood that this invention is not limited to the particular methods, constructs and reagents described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value and intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural references unless the context clearly dictates otherwise. Thus, for example, reference to "an enzyme" includes a plurality of such enzymes and reference to "the cDNA" includes reference to one or more cDNAs and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided might be different from the actual publication dates, which may need to be independently confirmed.

Definitions

The term "nucleic acid" as used herein refers to any polynucleotide, and is intended to encompass ribonucleic acids ("RNA"), including mRNA, and deoxyribonucleic acids ("DNA"), including genomic and cDNA. The term is also intended to encompass RNA or DNA having analogs or substitutions to the structure of the nucleic acid, provided the analogs or substitutions does not impede the ability to isolate and/or characterize the sequence of the desired region of the nucleic acid.

The term "primer" as used herein refers to a polymer of nucleotides capable of acting as a point of initiation of DNA synthesis when annealed to a nucleic acid template under conditions in which synthesis of a primer extension product is initiated, i.e., in the presence of four different nucleotide triphosphates and a polymerase in an appropriate buffer ("buffer" includes pH, ionic strength, cofactors, etc.) and at a suitable temperature. Generally, a primer will be between 12 and 100 nucleotides, more preferably between 15 and 80 nucleotides, and even more preferably between 18 and 50 nucleotides. The primer may be composed of naturally occurring and/or modified nucleotides, and the modified nucleotides may have a base substitution (e.g., an analog with improved binding), a modified internucleoside linkage, or a substitution of the ribose group.

A primer that hybridizes to a sequence, refers to a primer that is complementary to a strand of the nucleic acid and/or a strand of the adaptor. A primer that hybridizes to the coding region of a nucleic acid, or the corresponding strand of the adaptor, will have an "antisense" sequence, i.e., the primer will form Watson-Crick base pairing with the coding region. A primer that hybridizes to a sequence complementary to a sequence will have a "sense" sequence, i.e., it will have the same sequence as the coding region of the nucleic acid or the corresponding strand of the adaptor. For an amplification reaction, generally one primer hybridizes to the sense strand and a second primer hybridizes to a sequence complementary to the sense strand.

The term "oligo-dV primer" as used herein refers to a primer composed of non-deoxythymidine nucleotides, i.e. deoxyadenosine, deoxycytidine, and/or deoxyguanosine. The oligo-dV primers of the invention can consist of only one nucleotide (e.g., oligo-dC) or may be any combination of dA, dC or dG. The oligo-dV primers of the invention are preferably between 6 and 15 nucleotides in length, and more preferably from between 8 and 12 nucleotides in length.

The term "hybridization" as used herein, refers to the formation of a duplex structure by two single stranded nucleic acids due to complementary base pairing. Hybridization can occur between complementary nucleic acid strands or between nucleic acid strands that contain minor regions of mismatch. The melting temperature, or "Tm" measures stability of a nucleic acid duplex. The $T_m$ is the temperature (under defined ionic strength and pH) at which 50% of the base pairs have dissociated. Those skilled in the art of nucleic acid technology can determine duplex stability empirically considering a number of variables including, for example, the length of the nucleic acids, base composition and sequence, ionic strength, and incidence of mismatched base pairs.

The term "stringent hybridization conditions" as used herein refers to conditions under which only fully complementary nucleic acid strands will hybridize. Stringent hybridization conditions are well known in the art (see, e.g., Sambrook et al., 1985, Molecular Cloning—A Laboratory Manual, Cold Spring Harbor Laboratory, Cold Spring Harbor, N.Y.). Generally, stringent conditions are selected to be about 5 C. lower than the $T_m$ for the specific sequence at a defined ionic strength and pH. Typically, stringent conditions will be those in which the salt concentration is at least about 0.2 M at pH 7 and the temperature is at least about 60 C. Relaxing the stringency of the hybridizing conditions will allow sequence mismatches to be tolerated; the degree of mismatch tolerated can be controlled by suitable adjustment of the hybridization conditions.

The term "substantially complementary" as used herein refers to two single-stranded nucleic acids that are complementary except for minor regions of mismatch. Stable duplexes of substantially complementary sequences can be achieved under less stringent hybridization conditions. Those skilled in the art of nucleic acid technology can determine duplex stability empirically considering a number of variables including, for example, the length and base pair concentration of the nucleic acids, ionic strength, and incidence of mismatched base pairs.

The term "full-length" mRNA as used herein refers to an mRNA that encodes the entire translation region of an mRNA, including promoter or enhancer regions 5' of the translation start site. The term cam also used to encompass transcripts that comprise at least the start methionine of the coding region of an mRNA, i.e., a transcript that is comprised of the entire coding region of an mRNA.

EXAMPLES

Production of Full-length cDNA

The present invention provides an improved method for producing full-length cDNA comprising 1) relaxing the mRNA secondary structure, e.g., by adding an agent such as dimethyl sulfoxide (DMSO) to the first-strand synthesis reaction mixture and 2) utilizing a thermostable enzyme that exhibits 3' to 5' exonuclease activity for template driven enzymatic deoxynucleotide synthesis.

The protocol for producing a cDNA can use any variation known in the art, provided it is not contraindicative with the relaxation techniques used and/or the thermostable enzyme. In general, the first step in preparing a cDNA library is to purify the mRNA, which usually represents only about 1–'of the total RNA of the cell, the remainder being ribosomal RNA, transfer RNA, and several other RNA species. Many mRNAs from eukaryotic organisms have a poly(A) "tail," a tract of 50–150 adenosine residues at their 3' ends. A general practice for purifying mRNA from total cellular RNA involves specifically annealing, or binding, the poly(A) tail to oligo(dT), a single stranded DNA molecule of between about 12 and 30 consecutive dT residues (Jacobson, A. (1987) Meth. Enzymol. 152:254). Total cellular RNA can be incubated with a matrix to which oligo(dT) has been immobilized. Only RNA molecules containing poly(A) tails selectively anneal to the matrix.

Upon purification of poly(A)+ RNA, a double-stranded complementary DNA (cDNA) copy of this active RNA can be synthesized in vitro by two sequential enzymatic steps. An RNA-dependent DNA polymerase, known as a reverse transcriptase, is used to synthesize the first strand cDNA (complementary DNA), using the RNA as a template. Then, a DNA-dependent DNA polymerase copies the newly synthesized first cDNA strand to form a complementary second cDNA strand.

Relaxation of the secondary structure of the mRNA can be achieved using any physical or chemical means, as will be apparent to one skilled in the art upon reading the present disclosure. In a particular embodiment, the relaxation of the mRNA secondary structure is achieved via chemical means, e.g., the addition of a chemical such as DMSO or dimethylformamide at a concentration of about 5–20%, glycerol at a concentration of about 5–40%, formamide in a concentration about 5–10%, and betaine in a concentration about 0.5–2.2 M.

These chemicals are added in sufficient quantities to prevent occurrence of mRNA self-annealing, up to and including 10% of the final reverse transcription reaction volume.

In one embodiment, the invention provides the use of a polymerase having proofreading ability to increase the efficacy of the polymerase reaction in first strand synthesis and thus the production of full-length cDNAs. Examples of such enzymes include, but are not limited to, Pfu DNA polymerase, Tna DNA polymerase, Tma DNA polymerase or Tli DNA polymerase. Examples of such enzymes are those isolated from the organisms *Pyrococcus furiosus* (Pfu) (U.S. Pat. Nos. 5,948,663 and 5,866,395), *Thermotoga neapolitana* (Tne); *Thermotoga maritima* (Tma) (U.S. Pat. Nos. 6,077,664; 6,001,645; 5,948,614; and 5,939,301); and Pyrodictium species (U.S. Pat. No. 5,491,086).

These and other enzymes that have 3'–5' exonuclease (proofreading) activity are useful to practice the invention. However, Pfu is preferred because it does not have strand displacement activity.

Once synthesized, double-stranded cDNA can be inserted into a prepared cloning vector. To efficiently insert the cDNA into a cloning vector, the ends of the insert cDNA and the vector DNA molecules must be prepared such that they are compatible. For example, specialized linkers can be added to the cDNA ends, followed by digestion with the relevant enzyme to create single stranded protrusions that will anneal to corresponding ends in the vector. The insert and vector molecules are ligated together with T4 DNA ligase. The ligated vectors carrying their cDNA molecule inserts are then introduced into E. coli and screened.

Various approaches have been used to prepare the cDNA ends for vector insertion (Kimmel, A. R. and Berger, S. L. (1987) *Meth. Enzymol.* 152:307). Most have used the "linker" or "adapter" method described above. All methods using linkers require an additional step to protect the cDNA from being cleaved at adventitious restriction sites during digestion to create the cohesive ends (Wu, R., Wu, T. and Ray, A. (1987) *Meth. Enzymol.* 152:343). The protection is accomplished either by treating the cDNA with on site-specific methylases or by substituting a methylated dCTP analog for unmodified dCTP in the synthesis reactions.

The degradation of an oligonucleotide primer by a 3' exonuclease can be prevented by the use of modified nucleotides at the 3' terminus. For example, the use of dideoxynucleotides or deoxynucleotides having a phosphorothioate linkage at the 3' terminus of an oligonucleotide would prevent degradation by 3' exonucleases.

Identification and/or Validation of Full-length cDNAs

The methods of the present invention can also be used to validate and/or identify the presence of a full-length first strand cDNA. Such a method can be used in any conventional means for producing cDNA to determine whether or not the cDNA produced encompasses the 5' end of the transcript.

Following first strand synthesis of cDNA from the mRNA, the DNA:RNA hybrid molecule can be used as a template for a further reverse transcription reaction, using a mixture of detectably labeled oligo-dV primers to initiate the template driven enzymatic deoxyribonucleic acid synthesis. This mixture may contain a plurality of the same oligo-dV primer, or may contain oligo-dV primers of varying sequences.

The RNA:DNA hybrid is hybridized to a detectably labeled oligo-dV primer mixture under conditions sufficient for template driven enzymatic deoxyribonucleic acid synthesis to occur, wherein the primer results in additional production of hybrid sequences provided the deoxyribonucleic acid does not extend to the 5' end of the ribonucleic acid. The presence of labeled product following this second reverse transcription reaction is indicative of incomplete reverse transcription in the first reaction, i.e., a non-full-length cDNA in the RNA:DNA hybrid.

Synthetic oligonucleotides may be prepared by the method of Efimov, V. A. et al. (*Nucl. Acids Res.* (1982) 6875–6894), and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1–2 mM ATP, 1.7 pmoles γ32P-ATP (2.9 mCi/mmole), 0.1 mM spermidine, 0.1 mM EDTA.

Production of cDNA Libraries

The methods of the present invention can also be used to produce cDNA libraries having an increased percentage of inserts comprising the 5' end of a transcript, (e.g., has an increased percentage of inserts encoding at least the start methionine of an mRNA.) each library comprising size fractionated cDNAs preferably enriched for full-length mRNA sequences. The methods used to produce the cDNAs can comprise 1) comprising relaxing the mRNA secondary structure, e.g., by adding an agent such as dimethyl sulfoxide (DMSO) to the first-strand synthesis reaction mixture and utilizing a thermostable enzyme that exhibits 3' to 5' exonuclease activity for template driven enzymatic deoxynucleotide synthesis; 2) validating the presence of the 5' end of the first strand cDNA using the oligo-dV driven deoxynucleotide synthesis, as described above; or 3) a combination of the two techniques. Where validation techniques are used, the full-length cDNAs can be identified by the absence of fluorescence in the product, and products lacking such fluorescence can be cloned into a vector, thus enriching the population of cDNAs comprising a 5'-end in the library. The incomplete (non-full length) cDNA is labeled with biotin and can be selectively removed using immobilized streptavidin.

Once the cDNA is produced, any number of methods can be used to produce a cDNA library, as will be apparent to one skilled in the art upon reading the present disclosure. The following is a general example of techniques that may be used, and as such is not meant to be limiting.

The cDNAs may be size selected prior to introduction into a vector, or may be directly introduced to a vector following production of the cDNAs. For example, the blunt-ended, double-stranded cDNA can be fractionated by size using gel filtration through a column (0.3×14 cm) Sepharose 4B (Pharmacia Fine Chemicals, Piscataway, N.J.) or by ultracentrifugation in 5–20% glycerol gradient followed by fractionation of the gradient. The cDNA is retained and recovered by precipitation with 70% ethanol. Short (10–30 nucleotide) polymeric tails of deoxycytosine are added to the 3' termini of the cDNA using a reaction containing 0.2M potassium cacodylate, 25 mM Tris, pH 6.9, 2 mM dithiothreitol, 0.5 mM $CoCl_2$, 200 mM cDTP, 400 μg/ml BSA, and 40 units calf thymus terminal deoxynucleotide transferase for 5 min at 22° C. The reaction is extracted with phenol:chloroform, and small oligonucleotides are removed with three ethanol precipitations in the presence of ammonium acetate.

Following isolation, the cDNAs can be ligated to adaptor molecules that allow cloning, directional or not, into the vector of choice. In one particular embodiment, the restriction sites used in the adaptors, and thus in the introduction of the cDNA insert into a vector, have relatively long recognition sites (i.e., recognition sites of 8 or more residues). The use of adaptors and multiple cloning sites having longer recognition sites decreases the chance of the site occurring in a cDNA, and thus increases the chance that the cDNA will be inserted into the vector in its full-length form. Construction of suitable vectors containing the desired coding and control sequences employs standard ligation and restriction techniques that are well understood in the art.

Site-specific DNA cleavage is performed by treating with the suitable restriction enzyme (or enzymes) under conditions that are generally understood in the art, the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 µl of buffer solution. In the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° C. to 25° C. in 50 mM Tris pH 7.6, 50 mM NaCl, 6 mM MgCl$_2$, 6 mM DTT and 5–10 µM dNTPs. The Klenow fragment fills in at 5' sticky ends but eliminates protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

Ligations are performed in 15–50 µl volumes under the following standard conditions and temperatures: 20 mM Tris-Cl pH 7.5, 10 mM MgCl$_2$, 10 mM DTT, 33 µg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments," the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of Na$_{30}$ and Mg$^{-2}$ using about 1 unit of BAP or CIP per µg of vector at 60° C. for about one hour. In order to recover the nucleic acid fragments, the preparation is extracted with phenol/chloroform and ethanol precipitated. Alternatively, religation can be prevented in vectors that have been double digested by additional restriction enzyme digestion of the unwanted fragments.

Once the cDNA library has been constructed as described above it can be screened by conventional methods designed to quickly determine whether a particular clone contains the desired nucleic acid sequence. In general, libraries are usually screened by hybridization to nick-translated DNA and synthetic oligonucleotides, or using immunoreactivity-based assays, or by hybrid selection of mRNA and translation. Libraries are usually spread out on agarose plates, transferred to nitrocellulose filters and hybridized to labeled oligonucleotide probes complementary to a target sequence in the cDNA, or the target polypeptides are expressed and bound to labeled antibodies which recognize an epitope on a target polypeptide. In both instances, the label can be radioactive (e.g., 32P), fluorescent, biotinylated, and the like. When clones containing cDNA encoding the target polypeptide have been found, the cDNA can be readily isolated for larger scale expression, e.g., by cutting the cDNA from the vector and amplifying it using PCR. This step can be facilitated where restriction sites are available in the cDNA sequence or engineered in the flanking sequence of the vector.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Full-length cDNA Synthesis, Selection and Cloning

First Strand Synthesis

2 µl DMSO was added to 1.5 µg mRNA and the volume to 11 µl with water. The mixture was heated to 70° C. for 5 minutes, and then quick-chilled on ice. Contents were collected at the bottom of the tube by brief centrifugation. Primer mix was then added 0.75 µg in 1 µl water. Each primer mix was a combination of an antisense strand, 5'pCTCCAGTCGCGATCTAGAACTAGTC (SEQ ID NO:1) annealed equimolar to one of five sense strands:

```
5' pGACTAGTTCTAGATCGCGACTGGAGTTTTTTTTTTTTTTTTTVV (SEQ ID NO:2);

5' pGACTAGTTCTAGATCGCGACTGGAGTTTTTTTTTTTTTTTTVTV (SEQ ID NO:3);

5' pGACTAGTTCTAGATCGCGACTGGAGTTTTTTTTTTTTTTTVTTV (SEQ ID NO:4);

5' pGACTAGTTCTAGATCGCGACTGGAGTTTTTTTTTTTTTTVTTTV (SEQ ID NO:5);

and

5' pGACTAGTTCTAGATCGCGACTGGAGTTTTTTTTTTTTTTVVVVV (SEQ ID NO:6).
```

Each primer was gel-purified prior to dilution.

The following components were then added to the mRNA-primer mix: 4 µl 5× first strand buffer; 1 µl 0.1 M DTT;1 µl 10 mM methyl dNTP mix (10 mM each of dG, dA, dT and Methyl-dCTP); and 1 µl α-[$^{32}$P]dCTP (10 µCi/µl; Amersham). Contents were gently vortexed and collected by brief centrifugation. One µl of mut-MMLV-RT (200 u/µl)

was added gently and incubated at 42 C. for 1 hour. Following incubation, 0.5 µl pfu (Stratagene, 2.5 u/µl) were added, and the mixture incubated at 55 C. for 10 minutes. 0.5 µl mut-MMLV-RT (RnaseH minus MMLV (Moloney murine leukemia virus) reverse transcriptase from Stratascript by Stratagene) were added, and incubated at 42 C. for an additional 20 minutes. The temperature is then slowly brought to a final temperature of 55 C. over 20 minutes.

To assess the quantity, quality and average length of the synthesized first-strand cDNA, 0.5 µl sample of the reaction was added to 10.75 µl 200mM EDTA and 1.25 µl yeast tRNA (1 mg/ml) in a 1.5 ml microcentrifuge tube and mixed well.

For each sample a GF/C filter was labeled with an EtOH proof (VWR) marker, and 10 µl of the sample spotted onto each of the filters and let dry. The CPM for each sample on the dried filters was calculated to determine the overall count. The filters were washed for five minutes in 300 ml of cold 10% TCA and 1% sodium pyrophosphate and 1× in 75 ml of cold 100% EtOH while shaking. The filters were dried again to determine the TCA precipitable counts incorporated into the newly synthesized cDNA strand.

Non-full-length sequences were removed from the pools using primers complementary to the 3' end of the sense strand primers. Added to the mixture were:

4 µl 5× first strand buffer;

1 µl N1V5 (NVVVVV) 100 ng/µl;

3.5 µl Biotin-dATP 0.4 mM;

3.5 µl Biotin dCTP 0.4 mM;

3.5 µl dTTP 0.4 mM;

3.5 µl dGTP 0.4 mM; and

1 µl mut-MMLV RT.

The mixture was incubated at 37 C. for 30 minutes, then 1 µl 0.5M EDTA was added. The reaction contents were spun through a chromospin 1000 column to remove unincorporated nucleotides and excess primer. Following spinning, an equal amount of 2×M280 streptavidin binding buffer (Dynal) was added. The sample was incubated with 200 µl of prewashed M280 beads with agitation at 37 C. for 10 minutes and the supernatant removed.

To precipitate the first strand cDNA, one-half volume of 7.5 M NH$_4$Oac and 1 µl of glycogen (20 µg) was added followed by 2.5 volumes of 100% ethanol. The mixture was vortexed thoroughly and centrifuged at 14,000×g at room temperature for 15 minutes. The supernatant was carefully removed and the pellet gently rinsed with 200 µl of cold 70% ethanol, followed by another centrifugation for 2 min. at 14,000×g. The wash was repeated, and all of the ethanol removed. The pellet was allowed to dry for 5–10 minutes to evaporate residual ethanol.

Second Strand Synthesis

For second strand synthesis, the following were added to the first strand cDNA pellet:

4 µl 5× first strand buffer;

2 µl 0.1M DTT;

104 µl DEPC-treated water;

30 µl 5× second strand buffer;

4 µl 10 mM dNTP mix (unmethylated);

1 µl E. coli ligase (10 U/µl);

4 µl E. coli DNA polymerase I (10 U/µl); and

1 µl E. coli RNaseH (2 U/µl).

This was gently mixed, and the reaction incubated at 16 C. for 2hr. 2 µl (5 U/µl) of T4 DNA polymerase were added, and incubating continued at 16° C. for 5 minutes. The reaction mixture was then placed on ice and 10 µl of 0.5 M EDTA was added.

An equal amount of 2× dynal M280 streptavidin binding buffer was also added, and the reaction mixture was incubated with 100 ill of prewashed M280 beads with agitation at 37 C. for 10 min, and the solution extracted to a new tube. An equal volume of phenol:chloroform:isoamyl alcohol (25:24:1; Amersham) was added, the mixture vortexed thoroughly, and centrifuged at room temperature for 5 minutes at 14,000×g to separate the two phases. The upper, aqueous layer was carefully removed and transferred to a new 1.5 ml tube.

To precipitate the cDNA, one-half volume of 7.5 M NH$_4$Oac and 1 µl of glycogen (20 µg) was added followed by 2.5 volumes of 100% ethanol. The mixture was vortexed thoroughly and centrifuged at 14,000×g at room temperature for 15 minutes. The supernatant was carefully removed and the pellet gently rinsed with 200 µl of cold 70% ethanol, followed by another centrifugation for 2 min. at 14,000×g. The wash was repeated, and all of the ethanol removed. The pellet was allowed to dry for 5–10 minutes to evaporate residual ethanol. The cDNA pellet was resuspended in 70 µl of 1× TE buffer.

Iceu 1 Adapter Addition

An adaptor was added to the synthesized cDNAs to allow cloning of the cDNAs into an appropriate vector. The following reagents were added to the to 34 µl of cDNA:

10 µl 5× T4 ligase buffer;

1 µl of Iceu adapters (2 µg/µl) ("p"ggtagcga) (ptcgctaccttag);

5 µl of T4 DNA ligase; and

50 µl final volume.

The reaction mixture was mixed gently and incubated overnight at 16 C. The volume was then brought to 200 µl by adding 150 µl of DEPC water, and an equal volume of phenol:chloroform: isoamyl alcohol (25:24:1) was added and the mixture vortexed thoroughly and centrifuged at room temperature for 5 minutes at 14,000×g to separate the two phases. The upper, aqueous layer was carefully removed to a new 1.5 ml tube.

The cDNA with adaptor was precipitated by adding 1/2 volume 7.5 M NH$_4$OAc, 1 µl of glycogen (at 20 µg/µl) followed by 2.5 volumes of 100 % EtOH. The precipitation mixture was vortexed thoroughly and centrifuge at 14,000×g at room temperature for 15 minutes. The supernatant was carefully removed and the pellet rinsed gently 2× with 200 µl of cold 70% EtOH and centrifuged for 2 minutes to remove the EtOH. The pellet was air-dried for 5–10 minutes to evaporate residual EtOH, and the pellet resuspended in 40.5 µl DEPC water.

BpMI Digestion

The 40.5 µl cDNA/adaptor mixture

5 µl 10× buffer 3

0.5 µl 100× BSA

4 µl BpMI (New England Biolabs)

50 µl total volume

This was mixed gently and incubated at least 4–5 hrs at 37 C. The volume was then brought to 200 µl by adding 150 µl of DEPC water. An equal volume of phenol:chloroform:isoamyl alcohol (25:24:1) was added, the mixture vortexed thoroughly, and centrifuged at room temperature for 5 minutes at 14,000×g to separate the two phases. The upper, aqueous layer was carefully removed and transferred to a new 1.5 ml tube. One-half volume of 7.5 M NH$_4$Oac and 3.5 µl of yeast tRNA (1 µg/µl) were added, followed by 2.5 volumes of 100% ethanol. The mixture was vortexed thoroughly and centrifuged at 14,000×g at room temperature for 15 minutes. The supernatant was carefully removed and the pellet gently rinsed twice with 200 µl of 70% EtOH. Following rinsing, the pellet was centrifuged for 2 minutes at 14,000×g, and the supernatant removed. The pellet was air dried for 5–10 minutes to evaporate residual ethanol and resuspended in 70 µl of STE.

The cDNA was then sized using a Bio-Rad Poly-prep Chromatography Column was filled with 2 ml STE-equilibrated Sepharose. The sample was added to the column and allowed to drip through. STE was added to elute the cDNA, and the run-off collected in fractions. The amount of cDNA in each fraction was determined, and fractions having a significant concentration of cDNA precipitated.

Add 20 µg glycogen, 1/2 volume 7.5 M NH$_4$OAc and 2.5 volumes 100% EtOH. Precipitate for greater than three hours to overnight. Vortex the mixture thoroughly and centrifuge at 14,000×g at room temperature for 30 min. Wash with 200 µl cold 70% EtOH and air dry. Count the dry pellets.

Example 2

Creating a cDNA Library

The cDNA was then cloned into the vector pCMV$_{13}$ ICIS to create cDNA library using the methods of the invention.

The following components were added to a 1.5 ml microcentrifuge tube:

2 µl 5× DNA ligase buffer;

1 µl (25 ng/µl) of pCMV$_{13}$ ICIS (IceuF/BsgI cut);

10 ng cDNA;

water to bring the volume up to 9 µl ; and

1 µl of T4 DNA ligase (New England Biolabs, Beverly, Mass.).

Vortex gently to mix and quick-spin contents to bottom of the tube. The reaction was then incubated at room temperature for 2 hr.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of isolating a full-length cDNA, said method comprising:

contacting a ribonucleic acid molecule with a first primer under conditions sufficient for template driven enzymatic deoxyribonucleic acid synthesis to occur, whereby a hybrid molecule comprising said ribonucleic acid molecule hybridized to a first deoxyribonucleic acid molecule comprising the first primer is produced;

contacting the hybrid molecule with a detectably labeled oligo-dV primer under conditions sufficient for template driven enzymatic deoxyribonucleic acid synthesis to occur, wherein said labeled primer hybridizes to the ribonucleic acid and an additional hybrid molecule is produced when the first deoxyribonucleic acid does not extend to the 5' end of the ribonucleic acid;

isolating a hybrid molecule that does not contain the detectable label; and converting said unlabelled hybrid molecule to a double-stranded deoxyribonucleic acid molecule.

2. The method of claim 1, wherein said single-stranded ribonucleic acid molecule is a mRNA.

3. The method of claim 1, wherein the first primer is an oligo-dT primer.

4. The method of claim 1, wherein the first primer is a random primer.

5. The method of claim 1, wherein the oligo-dV primer is labeled with biotin.

6. The method of claim 1, wherein the oligo-dV primer is radioactively labeled.

7. The method of claim 1, wherein the oligo-dV primer is comprised of 4–12 nucleotides.

8. The method of claim 1, wherein said method further comprises introducing said double-stranded cDNA molecule into a vector.

* * * * *

UNITED STATES PATENT AND TRADEMARK OFFICE
CERTIFICATE OF CORRECTION

PATENT NO. : 6,509,175 B2
DATED : January 21, 2003
INVENTOR(S) : Gelnn K. Fu et al.

It is certified that error appears in the above-identified patent and that said Letters Patent is hereby corrected as shown below:

Column 3,
Line 5, please change "unlabelled" to -- unlabeled --.

Column 5,
Line 5, please change "internucleoside" to -- internucleotide --.

Column 6,
Line 4, please change "cam also used" to -- can also be used --.
Line 18, please change "contraindicative" to -- contraindicated --.

Column 8,
Line 45, please change "phenol:chloroform" to -- phenol chlorofrom --.

Column 16,
Line 28, please change "unlabelled" to -- unlabeled --.

Signed and Sealed this

Twenty-fourth Day of June, 2003

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: antisense strand of primer

<400> SEQUENCE: 1
ctccagtcgc gatctagaac tagtc                                    25

<210> SEQ ID NO 2
<211> LENGTH: 46
<212> TYPE: DNA
<213> ORGANISM: Artificial Sequence
<220> FEATURE:
<223> OTHER INFORMATION: sense strand of primer

<400> SEQUENCE: 2
gactagttct agatcgcgac tggagttttt tttttttttt ttttvv           46

<210> SEQ ID NO 3
<211> LENGTH: 47
<212> TYPE: DNA
<213> ORGANISM: Artificial Sequence
<220> FEATURE:
<223> OTHER INFORMATION: sense strand of primer

<400> SEQUENCE: 3
gactagttct agatcgcgac tggagttttt tttttttttt ttttvtv          47

<210> SEQ ID NO 4
<211> LENGTH: 48
<212> TYPE: DNA
<213> ORGANISM: Artificial Sequence
<220> FEATURE:
<223> OTHER INFORMATION: sense strand of primer

```
<400> SEQUENCE: 4
gactagttct agatcgcgac tggagttttt ttttttttt ttttvttv                48

<210> SEQ ID NO 5
<211> LENGTH: 49
<212> TYPE: DNA
<213> ORGANISM: Artificial Sequence
<220> FEATURE:
<223> OTHER INFORMATION: sense strand of primer

<400> SEQUENCE: 5
gactagttct agatcgcgac tggagttttt ttttttttt ttttvtttv               49

<210> SEQ ID NO 6
<211> LENGTH: 49
<212> TYPE: DNA
<213> ORGANISM: Artificial Sequence
<220> FEATURE:
<223> OTHER INFORMATION: sense strand of primer

<400> SEQUENCE: 6
gactagttct agatcgcgac tggagttttt ttttttttt ttttvvvvv               49
```